US 6,747,740 B1

(12) United States Patent
Leveille et al.

(10) Patent No.: US 6,747,740 B1
(45) Date of Patent: Jun. 8, 2004

(54) APPROACH TO SHORT MEASUREMENT PATH-LENGTH FLOW CELLS

(75) Inventors: Michael J. Leveille, Northbridge, MA (US); Joseph M. DeLuca, Mendon, MA (US)

(73) Assignee: Waters Investments Limited ( * ) Notice: Subject to any disclaimer, the term of this patent is extended or adjusted under 35 U.S.C. 154(b) by 0 days.

(21) Appl. No.: 09/702,513

(22) Filed: Oct. 31, 2000

(51) Int. Cl.[7] ............................................. G01N 21/05
(52) U.S. Cl. ........................................ 356/446; 356/246
(58) Field of Search ................................. 356/440, 246

(56) References Cited

U.S. PATENT DOCUMENTS

| | | | | |
|---|---|---|---|---|
| 3,552,864 A | * | 1/1971 | Shields | 356/246 |
| 4,580,901 A | * | 4/1986 | Goldsmith | 356/409 |
| 4,588,893 A | * | 5/1986 | Vidrine et al. | 356/246 |
| 5,003,174 A | * | 3/1991 | Dätwyler et al. | 356/246 |
| 5,905,271 A | * | 5/1999 | Wynn | 356/246 |

* cited by examiner

Primary Examiner—Richard A. Rosenberger
(74) Attorney, Agent, or Firm—Brian Michaelis; John Serio; Anthony J. Janiuk

(57) ABSTRACT

A photometric measurement flow cell having measurement path-lengths that can be adjusted down to less than 0.1 mm. The measurement path-length is controlled by both a common flow cell body and the dimensional parameters of a stepped sealing optical element. The stepped optical element includes a stem portion that can be made in various lengths to create a family flow cell measurement path-lengths. The replacement of one stepped element with another having a different stem length within the flow cell creates a reliable method to adjust the measured path-length of the flow cell.

15 Claims, 3 Drawing Sheets

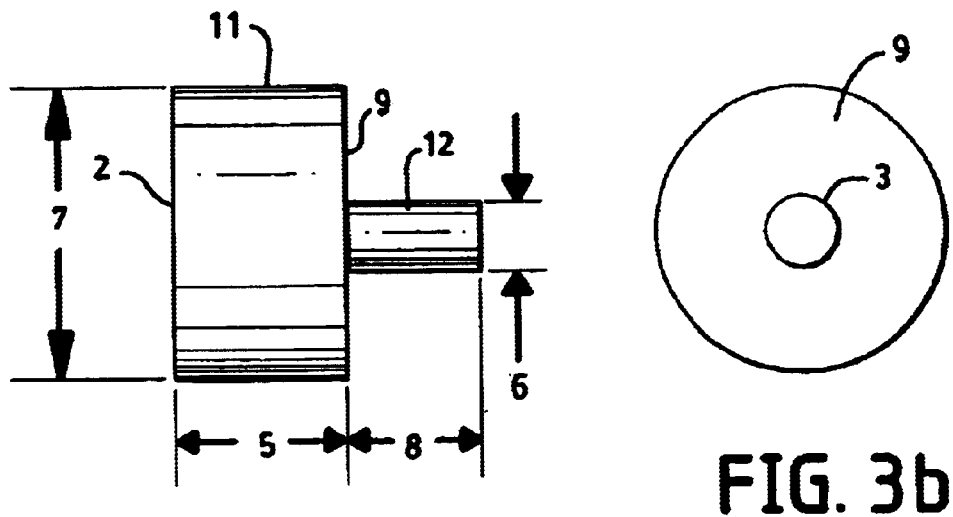
FIG. 3a  FIG. 3b
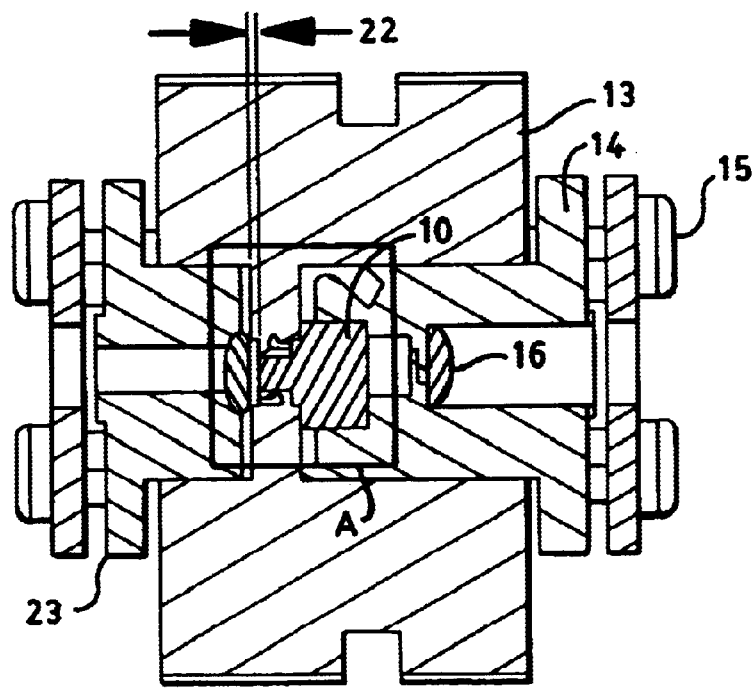
FIG. 4a

APPROACH TO SHORT MEASUREMENT PATH-LENGTH FLOW CELLS

FIELD OF INVENTION

The present invention relates to a method of creating a photometric measurement path-length flow cell and more particularly, to provide an adjustable path-length in a flow cell.

BACKGROUND OF THE INVENTION

The measurement of an analyte of interest by a photometric detector is dependent upon several parameters for the accurate analysis of the object of detection. The path-length of the object of interest through the flow cell is of importance in the accuracy and sensitivity of analysis. The determination of the accurate measurement of that path-length becomes essential in devices that have adjustable path-lengths. Several approaches to the determination of path-length in the prior art have been attempted with certain limitations.

For example, the Sonn-Tek adjustable flow cell, available from Sonntek, Inc. of New Jersey, and illustrated in FIG. 1, is configured to adjust for the desired path-length by the movement of one or two small glass rods by the mechanical movement of special screws that exert pressure upon the glass rods to reduce the path-length. The mechanism of increasing the path-length in the Sonn-Tek flow cell is by the internal cell pressure of the cell. Internal cell pressures of 250 psi or more are needed in order to back the above glass rod out when an increase in path-length is needed. A major disadvantage of this method of adjusting the path-length is that the user of the device has only an approximate indication of the measurement path-length. To calculate the true path-length, the user must iteratively rely on chemistries until they are confident that the flow cell has been adjusted correctly. An additional problem with this adjustable cell is the potential for contamination from unswept volumes due to the sealing mechanisms typically used on such cells. While this contamination problem may not be a major issue at high preparative flow rates, it becomes increasingly problematic at flow rates that are typical of analytical work. Another limitation of this device is that this type of flow cell is generally more difficult to rebuild and maintain than the standard non-adjustable cells.

Another attempt, illustrated in FIG. 2, has been to fashion flow cells where the desired critical measurement of the optical path-length and the fluidic path-length are the same and inherent with the design of the cell body. A severe limitation imposed by this approach is that each path-length requirement would need a different flow cell body to be machined. The fabrication of these short path-length flow cells are relatively expensive to machine. Additionally, for measurement path-length requirements that are shorter than approximately 1.0 mm, conventional machining methods become unreliable due to the thin cross sections involved. The fluidic connections are also problematic when the path-length is less than approximately 1.0 mm. That is, it is difficult getting a 1.0 mm internal diameter tubing to work with a 0.5 mm path-length cell without flow restriction.

Known implementations suffer limitations with respect to reliability, expense, sensitivity and accuracy.

SUMMARY OF THE INVENTION

The present invention provides a photometric measurement flow cell having measurement path-lengths that can be reliably, accurately, and inexpensively adjusted down to less than 0.1 mm.

According to the invention, path-length is controlled in a common flow cell body by dimensional parameters of a stepped sealing optical element. The stepped optical element of the present invention is made of an optical glass, which in the illustrative embodiment is a fused silica glass. The stepped optical element includes a stem portion that can be made in various lengths and utilized to create a family of flow cell measurement path-lengths. The replacement of one stepped element with another having a different stem length within the flow cell creates a reliable method to adjust the measurement path-length of the flow cell.

The adjustable path-length of the flow cell of the present invention provides many benefits over conventional adjustable path-length flow cells. The flow cell configured according to the present invention is no more difficult to rebuild and maintain than conventional analytical flow cells. Bandspreading is reduced when using the present invention at low flow rates, compared to the conventional adjustable path-length flow cells. The reliability of the measurement path-length is greatly increased. The potential for contamination from unswept volumes due to the conventional sealing methods in adjustable path-length flow cells is eliminated. The lack of complexity in the manufacturing of the adjustable path-length flow cell of the present invention greatly reduces its cost. The machining problems and complexities associated with conventional adjustable flow cell for path-lengths below 1.0 mm are avoided.

BRIEF DESCRIPTION OF THE DRAWINGS

The foregoing and other features and advantages of the present invention will be more fully understood from the following detailed description of illustrative embodiments, taken in conjunction with the accompanying drawings in which:

FIG. 3a illustrates a flow cell stepped element according to the present invention.

FIG. 3b shows a top view of the stepped element according to the present invention.

FIG. 4a shows a flow cell utilizing a stepped element according to the present invention.

FIG. 4b is an enlargement of a portion A of FIG. 4a.

DETAILED DESCRIPTION OF THE INVENTION

Figure 1:
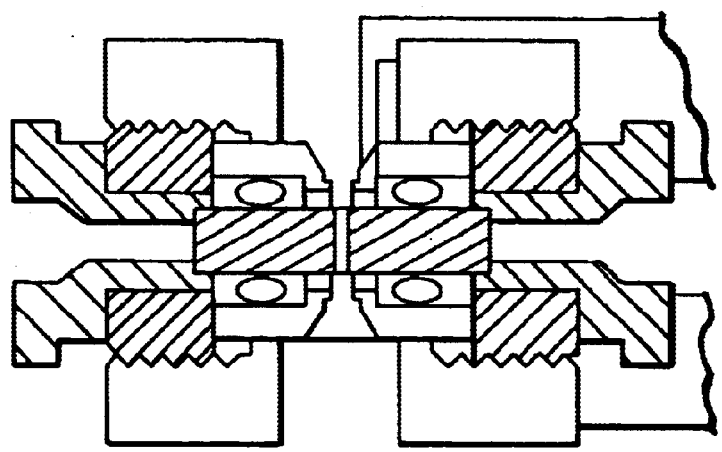
FIG. 1 shows a section drawing of an adjustable flow cell according to the prior art.
Figure 2:
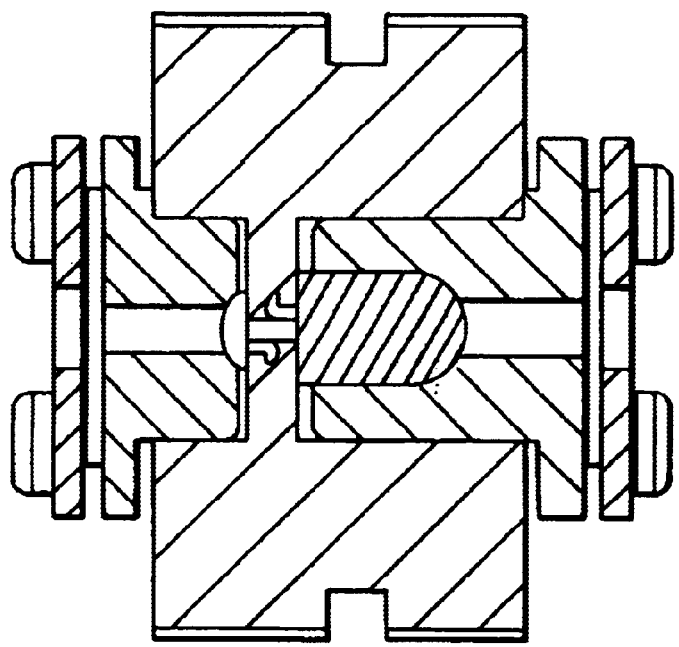
FIG. 2 shows a section drawing of non-adjustable flow cell according to the prior art.

Referring in detail to the drawings, a flow cell utilizing a stepped element of the present invention is shown in section in FIG. 4a. It comprises a cell body 13 that is formed from stainless steel, however, it can also be formed from materials such as titanium, peek or other materials known in the art that are inert to the sample substance and solvents utilized. The cell body 13 contains within it an element holder 14. The element holder contains within it an entrance lens 16. The entrance lens 16 is positioned within the element holder 14 adjacent to a stepped element 10. The stepped element 10 is configured of optical glass, which in the illustrative embodiment is fused silica glass. In alternative embodiments, optical glasses such as BK7, Sapphire, Flint and Crown glasses may be used. Additionally, numerous other optical materials known in the art may be used, provided that the material possesses sufficient optical qualities such as wavelength range, inertness to the sample substance and solvent utilized, and ease of manufacturing.

The stepped element 10, as described hereinafter with reference to FIG. 3a, is comprised of a base 11 and a stem 12. The base 11 has a base height 5 and the stem 12 has a stem length 8. Both the base height 5 and the stem length 8 can vary in size. In an illustrative embodiment the base 11 and the stem 12 are round in their configuration. In alternative embodiments, the stepped element 10 can be configured in various geometric forms according to the requirements of the element holder 14 and the entrance lens 16. The stem 12 and base 11 contain end surfaces 2 and 3 respectively, which in the illustrative embodiment is a plano optical surface. In alternative embodiments, the end surfaces 2 and 3 could be a spherical or aspherical surface. As illustrated in FIG. 3a and FIG. 3b the stem 12 of the stepped element 10 protrudes from the base 11 in varying degrees according to the stem length 8. The base 11 has a base diameter 7 that is in excess of a stem diameter 6. The increase of the base diameter 7 over that of the stem diameter 6 creates a sealing surface 9 on the stepped element 10. The actual numerical values for these dimensions can vary to suit a particular flow cell design. However, it is the stem length 8 that for a given flow cell will determine the measurement path-length. Virtually the only limitation in the stem length 8 would be manufacturing restrictions. These manufacturing restrictions can be avoided provided that the design of the stepped element 10 allows for adequate ratios of stem diameter 6 to stem length 8 to base diameter 7. The stem diameter 6 should be of minimal but sufficient size to convey a cone of light entering the flow cell without a decrease in brightness on the outer areas of the stepped element 10, therefore minimizing bandspreading.

Figure 4B:
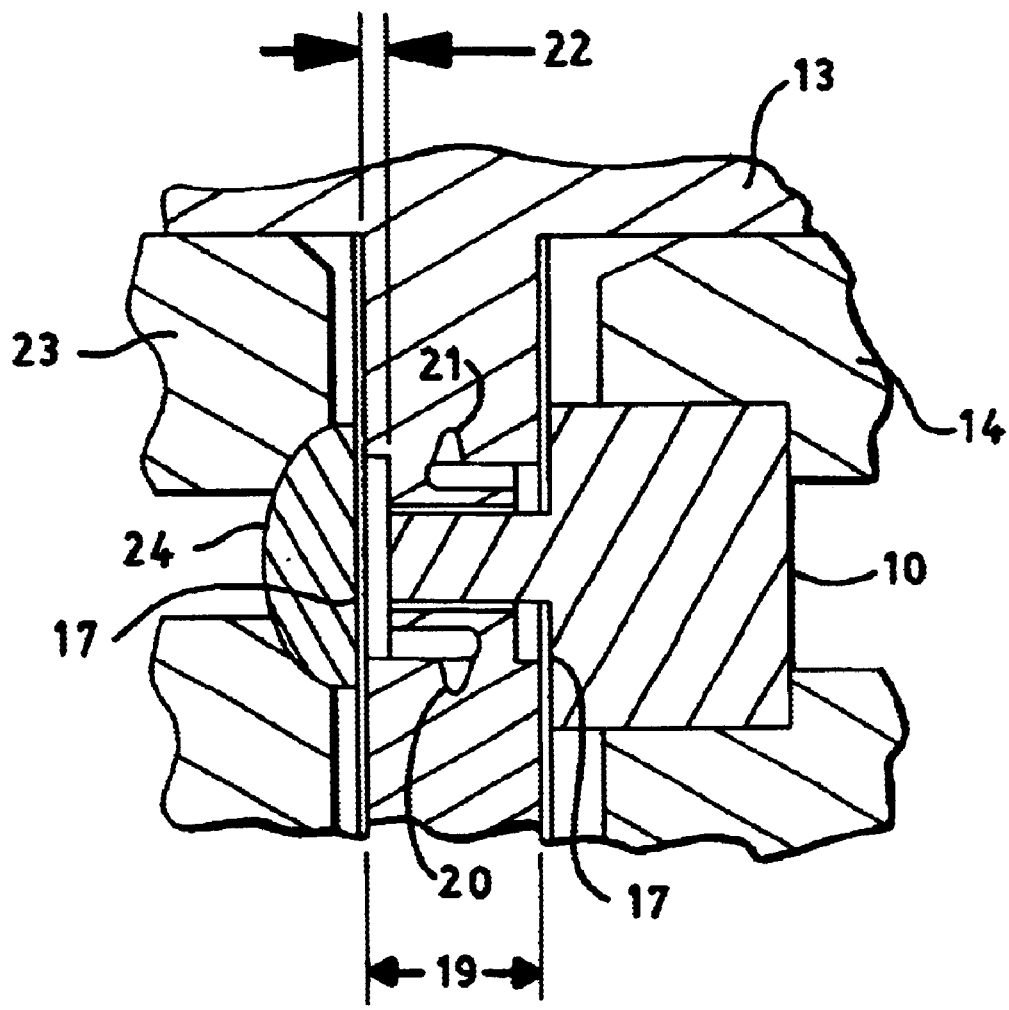

Referring now to FIGS. 4a and 4b, in the illustrative embodiment of the present invention, the element holder 14 is secured within the cell body 13 by a plurality of fastening bolts 15. The element holder 14 positions the stepped element 10 so that the stem 12 protrudes into a fluidic channel 19. The fluidic channel 19 has an inlet port 20 and an outlet port 21. The stem 12 of the stepped element 10 is positioned within the fluidic channel 19 between the inlet port 20 and the outlet port 21 creating a measurement path-length 22. The measurement path-length 22 can be varied by increasing or decreasing the stem length 8 of the stem 12. That is, a variable path-length flow cell is effected by providing a plurality of stepped elements 10 each having a different stem length 8. The fastening bolts 15 exert pressure upon the element holder 14, the sealing surface 9 of the stepped element 10 and upon a sealing gasket 17 causing stepped element 10 to be reliably sealed within the cell body 13 and against the fluidic channel 19.

As illustrated in FIG. 4b the cell body 13 contains a lens holder 23. The lens holder 23 is positioned within the cell body 13 opposite the element holder 14. The lens holder 23 contains an exit lens 24 within it. The exit lens 24 forms a wall of the fluidic channel 19. The exit lens 24 is positioned opposite the stepped element 10. The lens holder 23 is secured within the cell body 13 by the plurality of fastening bolts 15 that also fastens the element holder 14. The fastening bolts 15 exert pressure upon the lens holder 23, the exit lens 24, and a second sealing gasket 17 causing the exit lens 24 to be reliably sealed against the cell body 13 and the fluidic channel 19.

In an illustrative embodiment of the present invention a measurement path-length 22 of 0.5 mm can be achieved utilizing a cell body 13 having a typical measured path-length of 3.0 mm. A stepped element 10 as illustrated in FIG. 3 with the following corresponding measurements is used. The stem 12 would have a stem length 8 of 2.5 mm. The base height 5 would be 3.5 mm. The stem diameter 6 and the base diameter 7 would be 1.8 mm and 6.32 mm respectively. If the operator required 1.0 mm instead of the above 0.5 measurement path-length 22 then a stepped element 10 with a stem length 8 of 2.0 mm would be utilized.

Although the fused silica optical glass stepped element 10 described in the illustrative embodiment herein is of a round configuration it should be appreciated that other geometric shapes could be implemented such as square, rectangular, octagonal, hexagonal, or the like. Similarly, rather than a fused silica, the stepped element 10 could be effected by making the stepped element from other glass or plastic that possesses sufficient optical properties and is inert to the samples analyzed and the solvents used. Similarly, rather than having a base 11 and stem 12 concentric to one another, the stepped element 10 could be effected by making the stem 12 non-concentric to the base 11.

Although entrance lens 16 and exit lens 24 are present in the illustrative herein it should be appreciated that the entrance lens 16 and the exit lens 24 could just as well be windows. Similarly, the entrance lens 16 or entrance window need not be required. Similarly, rather than having a step element 10 within the entrance assembly, the stepped element 10 can be used within the exit assembly of the flow cell 13.

Although the stepped element 10 described in the illustrative embodiment herein is for a flow cell having only one stepped element 10, it should be appreciated that alternative embodiments may have a flow cell having multiple stepped elements 10.

Virtually any number of stepped elements having differing stem length dimensions could be provided for use with a common flow cell body to provide numerous variations in measurement path-length according to the invention.

The foregoing has been a description of an illustrative embodiment of the present invention. While several illustrative details have been set forth, such are only for the purpose of explaining the present invention. Various other changes, omissions and additions in the form and detail thereof may be made therein without departing from the spirit and scope of the invention.

What is claimed is:

1. A photometric measurement flow cell comprising:

a cell body having a first end and a second end;

a fluidic channel allowing the passage of fluids, contained within said cell body;

an element holder contained within said first end of said cell body wherein said element holder has a substantially planar sealing surface for receiving an element said substantially planar sealing surface of said element to be fixed in a non-adjustable manner;

a non-adjustable stepped element having a stem and a base, said stem having an end surface protruding into said fluidic channel creating a fixed, non-adjustable fluidic measurement pathlength and said base having a substantially planar sealing surface, said substantially planar sealing surface of said base fixedly abutting said substantially planar sealing surface of said non-adjustable stepped element to be sealably secured in a non-adjustable manner in said element holder;

said non-adjustable stepped element contained within said element holder and sealed within said cell body by a sealing gasket positioned between said substantially planar sealing surface of said non-adjustable stepped element and said substantially planar sealing surface of said cell body whereupon pressure exerted against said substantially planar sealing surface of said non-adjustable stepped element and said substantially planar sealing surface of said cell body cause said non-adjustable stepped element to be fixed and reliably sealed in a non-adjustable manner within said cell body with said stem protruding into said fluidic channel creating said fixed, non-adjustable fluidic measurement pathlength.

2. The photometric measurement flow cell according to claim 1, wherein said non-adjustable stepped element is formed of fused silica glass.

3. The photometric measurement flow cell according to claim 1, wherein said non-adjustable stepped element is formed of plastic.

4. The photometric measurement flow cell according to claim 1, wherein said non-adjustable stepped element is formed of crown optical glass.

5. The photometric measurement flow cell according to claim 1, wherein said non-adjustable stepped element is formed of flint optical glass.

6. The photometric measurement flow cell according to claim 1, wherein said non-adjustable stepped element is formed of BK7 optical glass.

7. The photometric measurement flow cell according to claim 1, wherein said non-adjustable stepped element is formed of sapphire optical glass.

8. The photometric measurement flow cell according to claim 1, wherein said end surface is plano optical surface.

9. The photometric measurement flow cell according to claim 1, wherein said end surface is a spherical optical surface.

10. The photometric measurement flow cell according to claim 1, wherein said end surface is an aspherical optical surface.

11. The photometric measurement flow cell according to claim 1, wherein said non-adjustable stepped element is circular in cross-section.

12. The photometric measurement flow cell according to claim 1, wherein said non-adjustable stepped element is a geometric configuration selected from the group consisting of a square, rectangular, octagonal, and hexagonal.

13. The photometric measurement flow cell according to claim 1, wherein said element holder contains within it an entrance lens.

14. The photometric measurement flow cell according to claim 1, wherein within said cell body is a lens holder containing an exit lens.

15. A method of creating an accurate fixed measurement path-length within a flow cell, which comprises:
providing a cell body having a fluidic channel allowing the passage of fluids within said cell body;
configuring an element holder contained within said cell body wherein said element holder has a substantially planar sealing surface for receiving an element said substantially planar sealing surface of said element to be fixed in a non-adjustable manner;
selecting a non-adjustable stepped element having a stem and a base, said stem having an end surface protruding into said fluidic channel creating a fixed, non-adjustable fluidic measurement pathlength, said base having a substantially planar sealing surface, said substantially planar sealing surface of said base fixedly abutting said substantial planar sealing surface of said non-adjustable stepped element to be sealably secured in a non-adjustable manner in said element holder, a length of said stem being selected to increase or decrease said fixed, non adjustable fluidic measurement pathlength; and
fastening said non-adjustable stepped element within said element holder with a sealing gasket positioned between said substantially planar sealing surface of said non-adjustable stepped element and said substantially planar sealing surface of said cell body whereupon pressure exerted against said substantially planar sealing surface of said non-adjustable stepped element and said substantially planar sealing surface of said cell body cause said non-adjustable stepped element to be fixed and reliably sealed in a non-adjustable manner within said cell body with said stem protruding into said fluidic channel creating said fixed, non-adjustable fluidic measurement pathlength.

\* \* \* \* \*